(12) United States Patent
Davies et al.

(10) Patent No.: US 6,399,311 B2
(45) Date of Patent: Jun. 4, 2002

(54) COMPOSITIONS, KITS, AND METHODS FOR HYDRODYNAMIC STRESS-RELATED REGULATION OF GENE EXPRESSION

(75) Inventors: Peter F. Davies, Haverford; Denise C. Polacek, Wynnewood, both of PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 09/783,836

(22) Filed: Feb. 14, 2001

Related U.S. Application Data (63) Continuation of application No. PCT/US99/18014, filed on Aug. 13, 1999.
(60) Provisional application No. 60/096,624, filed on Aug. 14, 1998.

(51) Int. Cl.[7] .................................................. C12Q 1/68
(52) U.S. Cl. ........................................ 435/6; 536/24.31
(58) Field of Search ........................... 435/6; 536/24.31

(56) References Cited

U.S. PATENT DOCUMENTS 5,514,545 A * 5/1996 Eberwine
6,225,084 B1 * 5/2001 Falb et al.

OTHER PUBLICATIONS

Barbee et al., 1995, Am. J. Physiol. 268:H1765–H1772.*
Davies et al., 1986, Proc. Nat. Acad. Sci. USA 83:2114–2118.*
Davies, 1995, Physiol. Rev. 75:519–560.*
Davies et al., 1995, J. Biomech. 28:1459–1469.*
Davies et al., 1997, Ann. Rev. Physiol. 59:527–549.*
DePaola et al., 1992, Arterioscler. Thromb. 12:1254–1257.*
DePaola et al., 1999, Proc. Natl. Acad. Sci. USA 96:3154–3159.*
Dewey et al., 1981, J. Biomech. Eng. 103:177–188.*
Eberwine et al., 1992, Methods in Enzymology 216:80–100.*
Martin–Mondiere et al., 1989, ASAIO Trans. 35:288–290 (Abstract only).*
McKinsey et al., 1995, FASEB J. A343 (Abstract only).*
Nagel et al., 1994, J. Clin. Invest. 94:885–891.*
Ohtsuka et al., 1993, Biochem. Biophys. Res. Comm. 193:303–310.*
Olesen et al., 1988, Nature, 331:168–170.*
Ranjan et al., 1993, Biochem. Biophys. Res. Comm. 196:79–84.*
Zarins et al., 1983, Circ. Res. 53:502–514.*

* cited by examiner

*Primary Examiner*—James Ketter
(74) *Attorney, Agent, or Firm*—Akin, Gump, Strauss, Hauer & Feld, L.L.P.

(57) ABSTRACT

Compositions, kits, and, methods for identifying genes, expression of which is spatially regulated in response to phenomena related to cellular hydrodynamic stress are disclosed.

26 Claims, 8 Drawing Sheets

| Regions | Location | Shear stress gradient (slope of stress curve) |
|---|---|---|
| 1 | Between lines a and b | 192 dynes/cm2 cm |
| 2 | Between lines b and c | 179 dynes/cm2 cm |
| 3 | Between lines c and d | 16 dynes/cm2 cm |
| 4 | To the right of line d | negligible |

COMPOSITIONS, KITS, AND METHODS FOR HYDRODYNAMIC STRESS-RELATED REGULATION OF GENE EXPRESSION

CROSS-REFERENCE TO RELATED APPLICATIONS

This application is a continuation of International Patent Application No. PCT/US99/18014 (Publication No. WO 00/09750, filed on Aug. 13, 1999), which is entitled to priority pursuant to 35 U.S.C. §119(c), and to U.S. Provisional Patent Application No. 60/096,624, filed on Aug. 14, 1998.

BACKGROUND OF THE INVENTION

Atherosclerosis, a disease of arteries that is responsible for most cardiovascular-related morbidity and mortality, develops in predictable regions of the arterial tree that correlate with complex patterns of blood flow. Although many atherosclerotic lesions are mild and cause little harm, those that progressively obstruct the passage of blood may reduce oxygen delivery to levels below the needs of the tissue (e.g., angina pain when coronary arteries are affected) or precipitate an acute ischemia (e.g., heart attack, stroke) when blood clots form on a destabilized lesion surface. Another catastrophic consequence of advanced lesions is the weakening of the artery wall, leading to pressure-induced ballooning (aneurysm) and potential rupture. It has long been recognized that hemodynamics determines the location of lesions. Local vessel geometry (e.g., arterial branching and curvatures), and constraint of vessel motion by surrounding tissues (e.g., coronary arteries) lead to flow instabilities and separations that correlate with sites of lesion development.

The one-cell thick layer at the interface between flowing blood and the artery wall is called the endothelium. Two decades of intense research have shown that the endothelium, rather than being a simple passive barrier, is instead both i) a multifunctional effector of systemic and vessel wall biology, and ii) an exquisitely sensitive responder to the local environment. The endothelium is directly exposed to the hemodynamic shear stresses associated with all of the different flow characteristics found in the circulation.

Endothelial cell responses to the hemodynamic environment are frequently heterogeneous. Prominent examples are the expression of VCAM-protein in vivo (Walpola et al., 1995, Arterioscler. Thromb. Vasc. Biol. 15:2–10) and in vitro (Ohtsuka et al., 1993, Biochem. Biophys. Res. Comm. 193:303–310), VCAM-1 mRNA expression in vivo (McKinsey et al., 1995, FASEB J. A343), ICAM-1 protein expression in vivo (Walpola et al., 1995, Arterioscler. Thromb. Vasc. Biol. 15:2–10) and in vitro (Nagel et al., 1994, J. Clin. Invest. 94:885–891), elevation of intracellular calcium ($[Ca^{2+}]_i$) measured in vitro (Geiger et al., 1992, Am. J. Physiol. 262:C1411–C1417; Shen et al., 1992, Am. J. Physiol. 262:C384–C390) and in vivo (Falcone et al., 1993, Am. J. Physiol. 264:H653–659), induction of synthesis and nuclear localization of c-fos in vitro (Ranjan et al., 1993, Biochem. Biophys. Res. Comm. 196:79–84), expression of major histocompatibility complex (MHC) antigens in vitro (Martin-Mondiere et al., 1989, ASAIO Trans. 35:288–290), inhibition of endothelial cell division in vitro (Ziegler et al., 1994, Arterioscler. Thromb. 14:636–643), and re-localization of the Golgi apparatus and microtubule organizing center (MTOC) in vitro (Coan et al., 1993, J. Cell Sci. 104:1145–1153). In each of these cases, high levels of response in one cell or a group of cells are accompanied by absent or diminished responses in adjacent cells of the same endothelial monolayer despite exposure to a substantially identical bulk flow field in vitro, or location in a predicted uniform hemodynamic environment in vivo.

In vitro, nominal flow characteristics are defined by the geometry of the experimental system (e.g., flow tube, parallel plate, cone and plate, etc.). The average wall shear stress and shear stress gradient values can be accurately estimated or directly measured (Dewey et al., 1981, J. Biomech. Eng. 103:177–188; Davies et al., 1986, Proc. Nat. Acad. Sci. USA 83:2114–2118; Olesen et al., 1988, Nature 331:168–170; DePaola et al., 1992, Arterioscler. Thromb. 12:1254–1257). Although the flow characteristics are more complex in vivo, average shear stress values can be estimated from vessel geometry and flow rates (Zarins et al., 1983, Circ. Res. 53:502–514). Such measurements demonstrate that although all of the cells in a given region of the monolayer are estimated to be subject to very similar shear stresses calculated from bulk flow characteristics, there are substantial cell-to-cell differences in acute and chronic responses to flow. If, as a significant number of experiments demonstrate, the responses are related to hemodynamic forces, it has not been determined what accounts for the heterogeneous responses.

In vitro flow chamber models of disturbed and undisturbed blood flow as described herein have recently been used to identify regionally defined differential expression of connexin43, and early response genes (DePaola et al., 1999, Proc. Natl. Acad. Sci. USA, 96:3154–3159; Nagel et al., Arterioscler. Thromb. Vasc. Biol., In press.) In regional differential gene expression studies during flow in vitro, endothelial cells are typically isolated by scraping the regions of interest. If enough cells are recovered, quantitative estimates of regional up- or down-regulation of gene expression (i.e., an average from all of the cells isolated from a particular location) can be made by northern blot analyses using specific nucleic acid probes for each gene of interest.

A useful alternative for analyzing the smaller numbers of cells typically present in defined hemodynamic regions is differential-display PCR (ddPCR; Liang et al., 1992, Science, 257:967–971), which uses reverse-transcription PCR (RT-PCR) to amplify all expressing genes in the cell population. This allows evaluation of differential expression of multiple genes when PCR products derived from cells in different hemodynamic regions are displayed together (e.g., as in Topper et al., 1996, Proc. Natl. Acad. Sci. USA, 93:10417–10422). Although ddPCR can be imprecise for quantitation of expression, this method has been used to identify differentially-expressed genes (e.g., Topper et al., 1997, Proc. Natl. Acad. Sci. USA, 94:9314–9319; Topper et al., 1997, J. Clin. Invest., 99:2942–2949; Topper et al., 1997, Proc. Natl. Acad. Sci. USA, 94, 9314–9319).

Although regional differential gene expression studies as described above are of value, the hemodynamic effects which modulate endothelial gene expression through spatial and temporal shear-stress relationships are ultimately defined locally at the surface of individual endothelial cells. Surface topographies, and consequently the magnitudes and gradients of shear-stresses, vary considerably from cell to cell (Barbee et al., 1995, Am. J. Physiol., 268:H1765–H1772). Differences in hemodynamic signaling and gene expression that have been observed from region to region and from cell to cell in endothelium (both in culture and in tissues) are likely to arise from microscopic topographic differences at the interface of the fluid and the cell surface. Examples of such heterogeneity include variable expression of endothelial vascular cell adhesion molecule-1 and intercellular adhesion molecule-1 proteins from cell to cell in vivo (Walpola et al., 1995, Arterioscler. Thromb. Vasc. Biol., 15:2–10 ; Nakashima et al., 1998, Arterioscler. Thromb. Vasc. Biol., 18:842–851) and in vitro (Nagel et al., 1994, J. Clin. Invest., 94:885–91), the elevation of intracellular calcium measured in vitro (Geiger et al., 1992, Am. J. Physiol., 262:C1411–1417; Shen et al., 1992, Am. J. Physiol., 262:C384–C390) and in vivo (Falcone et al., 1993 Am. J. Physiol., 264:H653–H659), the induction of synthesis and nuclear localization of c-Fos in vitro (Ranjan et al., 1993, Biochem, Biophys. Res. Commun., 196:79–84), and the expression of major histocompatibility complex antigens in vitro (Martin-Mondiere et al., 1989, ASAIO Trans., 35:288–290). In all of these studies, highly variable responses were observed in adjacent cells of the same endothelial monolayer exposed to a nominally identical flow field.

Two inter-related mechanisms may explain cell-to-cell differences in acute and chronic responses to hydrodynamic forces. First, there may be differential expression or sensitivity of mechano-sensing or transduction systems in the endothelial cells, ranging from a complete absence to supersensitivity. Second, the shear stresses and shear stress gradients acting on the cells may be heterogeneous because of differences in the detailed cell surface topography. Atomic force microscopy (AFM) and computational fluid dynamics (CFD) have been used to detail the geometry of living endothelial cell surfaces in vitro and in situ and to calculate the sub-cellular localized force distribution (Barbee et al., 1995, Am. J. Physiol. 268:H1765–H1772; Davies, 1995, Physiol. Rev. 75:519–560; Davies et al., 1997, Ann. Rev. Physiol. 59:527–549). Results of these studies indicated that microscopic hydrodynamic forces acting on individual endothelial cells vary considerably from cell to cell and within different regions of a single cell. It appears that, both in vivo and in vitro, differential responsiveness to macroscopically uniform shear stresses occurs because of microscopic heterogeneities. These studies assume importance in view of the complex flow fields associated with atherogenesis, and address the fundamental basis of atherosclerotic focal origin, lesion initiation, and progression.

An important implication of these findings is that expression of a limited number of genes in even only a few endothelial cells can dominate vascular physiology and vascular pathogenesis. However, the identity of such genes can be complicated by "dilution" of mRNA transcribed from such genes by more numerous mRNA species, particularly when the pool of cells from which mRNA is isolated includes only a few "dominant" cells.

Advances in single cell and mRNA amplification techniques and methods of obtaining quantitative profiles of gene expression (e.g., transcriptional profiles) including the use of gene arrays for high throughput analyses now allow one to address endothelial heterogeneity in a very detailed (e.g., single cell and small groups of cells) yet comprehensive (multiple genes, high-throughput) approach. However, little is currently known about the genes involved in mediating the heterogeneous responses of endothelial cells to hemodynamic forces. Thus, there is an unmet need in the art for methods and compositions related to focal hydrodynamic stress-related regulation of gene expression which are useful in the development of methods for the prevention and treatment of atherosclerosis and other cardiovascular diseases in humans. The present invention satisfies those needs by providing the means to characterize the gene expression profile(s) of a single cell or small groups of cells present in a local hemodynamic environment that promotes susceptibility to atherosclerosis in vivo, or simulates in vitro the flow disturbances associated with atherosclerosis.

BRIEF SUMMARY OF THE INVENTION

The invention includes a method of identifying a gene, expression of which is regulated by hydrodynamic stress. The method comprises a) subjecting a first vascular endothelial cell of a mammal to hydrodynamic stress; b) thereafter assessing the level of expression of the gene in the cell, and c) comparing the level of expression of the gene in the first cell with the level of expression of the same gene in a second vascular endothelial cell of the mammal, the second cell being subjected to different hydrodynamic stress, whereby a difference between the level of expression of the gene in the first cell and the level of expression of the gene in the second cell is an indication that the gene is regulated by hydrodynamic stress.

In one aspect, the cell is subjected to hydrodynamic stress using an in vitro flow chamber.

In a preferred embodiment, the flow chamber is capable of generating a hydrodynamic stress flow field having spatially defined microheterogeneity.

In another aspect, the microheterogeneity results in different hydrodynamic stresses exerted from one cell to another or from one part of a cell to another part of a cell in the flow chamber.

In one embodiment, the mammal is a human.

In one aspect, hydrodynamic stress is exerted in an amount from about 0 dyn/cm$^2$ to about 100 dyn/cm$^2$.

In another aspect, the hydrodynamic stress is exerted for at least about several seconds.

In one embodiment, the cell is a single cell isolated in vivo.

In a preferred embodiment, the cell is an arterial endothelial cell.

In another embodiment, the cell is a group of cells isolated in vivo.

In yet another embodiment, the cell is a single cell isolated in vitro from a confluent monolayer.

In one aspect, the cell is one of a group of cells isolated in vitro from a confluent monolayer.

In a preferred embodiment, the level of expression of the gene is assessed using amplified antisense RNA in combination with northern blotting or a microarray technique.

In one aspect, the level of expression of the gene is assessed in a single endothelial cell.

In another aspect, the level of expression of the gene is assessed in one of a group of endothelial cells.

In yet another aspect, the level of expression of the gene is compared by transcriptional profiling following one of northern blotting and microarray analysis using one of a radiolabeled probe, a fluorescent probe and a label.

In a further aspect, the levels of expression of a plurality of genes are compared. The invention also includes a method of identifying a nucleic acid comprising a hydrodynamic stress regulation (HSR) region. The method comprises a) subjecting a first vascular endothelial cell of a mammal to hydrodynamic stress;

b) thereafter assessing the level of expression of the nucleic acid in the cell, and c) comparing the level of expression of the nucleic acid in the first cell with the level of expression of the same nucleic acid in a second vascular endothelial cell of the mammal, the second cell being subjected to different hydrodynamic stress, whereby a difference between the level of expression of the nucleic acid in the first cell and the level of expression of the nucleic acid in the second cell is an indication that the nucleic acid comprises a HSR region.

In one embodiment, the cell is subjected to hydrodynamic stress using an in vitro flow chamber capable of generating a hydrodynamic stress flow field having spatially defined microheterogeneity.

In another embodiment, the level of expression of the nucleic acid is assessed using amplified antisense RNA from a single endothelial cell.

Also included in the invention is a method of identifying a nucleic acid comprising an HSR region. The method comprises a) comparing the sequence of a first nucleic acid with the sequence of a second nucleic acid comprising an HSR region, and b) identifying a region of the first nucleic acid which is homologous to the HSR region of the second nucleic acid, whereby a nucleic acid comprising a HSR region is identified.

Furthermore, the invention includes a method of identifying a hydrodynamic stress responsive protein. The method comprises a) subjecting a first vascular endothelial cell of a mammal to hydrodynamic stress; b) thereafter assessing the level of expression of a nucleic acid in the first cell, and c) comparing the level of expression of the nucleic acid in the first cell with the level of expression of the same nucleic acid in a second vascular endothelial cell of the mammal, the second cell being subjected to different hydrodynamic stress, whereby a difference between the level of expression of the nucleic acid in the first cell and the level of expression of the nucleic acid in the second cell is an indication that the nucleic acid encodes a hydrodynamic stress responsive protein, and d) identifying a protein encoded by the nucleic acid, whereby a hydrodynamic stress responsive protein is identified.

In one embodiment, the cell is subjected to hydrodynamic stress using an in vitro flow chamber capable of generating a hydrodynamic stress flow field having spatially defined microheterogeneity.

In another embodiment, the level of expression of the nucleic acid is assessed in a single endothelial cell.

The invention also includes an array of nucleic acids comprising an HSR region, wherein at least one of the nucleic acids is selected by a method of the invention.

Additionally, the invention includes, a kit for carrying out a method of the invention. The kit comprises a) an instructional material; b) a reagent for use in amplified antisense RNA; c) a reagent for use in northern blotting or microarray analysis, and d) a radiolabeled or fluorescent probe.

BRIEF DESCRIPTION OF THE SEVERAL VIEWS OF THE DRAWINGS

The foregoing summary, as well as the following detailed description of the invention, will be better understood when read in conjunction with the appended drawings.

FIGS. 3A, 3B, and 3C depict a flow chamber and a shear stress distribution gradient for in vitro studies of regionally-defined hemodynamics.

FIGS. 4A, 4B, and 4C show a pair of images depicting cooled, living endothelial cells labeled with a nuclear fluorescent stain in situ at the surface of a mammalian (swine) artery and a graph depicting a transcriptional profile of one of the endothelial cells.

DETAILED DESCRIPTION OF THE INVENTION

The present invention relates to methods and compositions useful for determination of hydrodynamic mechanisms of focal gene expression in endothelial cells in vivo and in vitro. The methods of the invention take advantage of the precise spatial control of hydrodynamic forces attainable in vitro and the physiological relevance of in vivo methods. The methods and compositions of the invention are essential for identifying the significance of cell-experienced hydrodynamic force heterogeneity at the level of gene expression. The methods of the present invention include methods for identifying genes, the expression of which is regulated by hydrodynamic stress. The methods and compositions of the present invention will lead to the identification of new genes useful in the development of treatments and therapies for atherosclerosis which have been revealed by large mRNA profile data banks from athero-susceptible regions of arteries generated using the methods of the invention.

Definitions

As used herein, the articles "a" and "an" are used to refer to one or to more than one (i.e., to at least one) of the grammatical object of the article. By way of example, "a cell" means one cell or more than one cell.

As used herein, a hydrodynamic stress sensor (HSS) protein is a protein of a cell which exerts a regulatory activity upon a biological molecule when the cell is subjected to hydrodynamic stress. The biological molecule may, for example, be a protein or a nucleic acid. The regulatory activity may, for example, be activation, inactivation, chemical modification (e.g., phosphorylation), or induction of transcription, or translation.

As used herein, a "hydrodynamic stress regulation (HSR) region" of a nucleic acid is a portion of the nucleic acid with which an HSS interacts, wherein the interaction of the HSS with the region in a cell subjected to hydrodynamic stress differs from the interaction of the HSS with the region in a cell subjected to different hydrodynamic stress (e.g., a cell not subjected to hydrodynamic stress).

As used herein, a "hydrodynamic stress responsive protein" is a protein which exhibits a different activity or a different level of activity when a cell which comprises the protein is subjected to hydrodynamic stress, relative to when the cell is subjected to different hydrodynamic stress.

By describing two polynucleotides as "operably linked" is meant that a single-stranded or double-stranded nucleic acid moiety comprises the two polynucleotides arranged within the nucleic acid moiety in such a manner that at least one of the two polynucleotides is able to exert a physiological effect by which it is characterized upon the other. By way of example, a promoter operably linked to the coding region of a gene is able to promote transcription of the coding region.

As used herein, the term "antisense" refers to a nucleic acid polymer, at least a portion of which is complementary to a nucleic acid which is present in a normal cell or in an affected cell. The antisense oligonucleotides of the invention preferably comprise between about fourteen and about fifty nucleotides. More preferably, the antisense oligonucleotides comprise between about twelve and about thirty nucleotides. Most preferably, the antisense oligonucleotides comprise between about sixteen and about twenty-one nucleotides. The antisense oligonucleotides of the invention include, but are not limited to, phosphorothioate oligonucleotides and other modifications of oligonucleotides. Methods for synthesizing oligonucleotides, phosphorothioate oligonucleotides, and otherwise modified oligonucleotides are known in the art (U.S. Pat. No. 5,034,506; Nielsen et al., 1991, Science 254:1497).

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

As used herein, an "instructional material" includes a publication, a recording, a diagram, or any other medium of expression which can be used to communicate the usefulness of the composition of the invention for performing a method of the invention. The instructional material of the kit of the invention may, for example, be affixed to a container which contains a composition of the invention or be shipped together with a container which contains such a composition. Alternatively, the instructional material may be shipped separately from the container with the intention that the instructional material and the composition be used cooperatively by the recipient.

The term "substantially purified" describes a compound, e.g., a protein or polypeptide which has been separated from components which naturally accompany it. Typically, a compound is substantially pure when at least 10%, more preferably at least 20%, more preferably at least 50%, more preferably at least 60%, more preferably at least 75%, more preferably at least 90%, and most preferably at least 99% of the total material (by volume, by wet or dry weight, or by mole percent or mole fraction) in a sample is the compound of interest. Purity can be measured by any appropriate method, e.g., in the case of polypeptides by column chromatography, gel electrophoresis or HPLC analysis. A compound, e.g., a protein, is also substantially purified when it is essentially free of naturally associated components or when it is separated from the native contaminants which accompany it in its natural state.

As used herein, an "essentially pure" preparation of a particular protein is a preparation wherein at least about 95%, and preferably at least about 99%, by weight, of the protein in the preparation is the particular protein.

As used herein, a "functional" biological molecule is a biological molecule in a form in which it exhibits a property by which it is characterized. A functional enzyme, for example, is one which exhibits the characteristic catalytic activity by which the enzyme is characterized.

As used herein, a cell "naturally" expresses a protein if a cell which exists in nature expresses the protein.

Description

Initiation and progression of focal atherosclerotic lesions have been associated with regions of disturbed blood flow, where endothelial morphology presumably mirrors local hemodynamic forces. Recent studies have demonstrated that lumenal surface geometry of vascular endothelial cells varies significantly within the apparently homogeneous endothelial monolayer. Consequently, the distribution, at a cellular or sub-cellular scale, of hemodynamic shear stresses over the lumenal surface varies significantly. Some vascular endothelial cells appear not to be affected by local hemodynamics, while vascular endothelial cells located very close to these cells do appear to be affected.

As described herein, there is significantly heterogeneous gene expression among vascular endothelial cells, and this heterogeneous gene expression is regulated by shear stress experienced by a cell. This was demonstrated by analysis of gene expression in single cells, as well as groups of cells, removed from selected hemodynamic locations of attached endothelia subjected to fluid flow in vitro and in vivo. A most recent example of differential gene and protein expression as a function of hemodynamic environment and one which uses the in vitro flow chamber described herein is described in DePaola et al. (1999, Proc. Natl. Acad. Sci. USA 96:3154–3159). Small regions of cells in a contiguous monolayer regionally expressed the gap junctional protein connexin43 as a function of the local fluid dynamic environment.

Disturbed flow regions are identified in humans and other mammals in vivo by magnetic resonance (MR) imaging or other non-invasive imaging techniques, and in tissue cultures using primary and early passage cultures of human endothelial cells and passaged cultures of endothelia of other species. Micropipet aspiration is used to isolate single cells for mRNA amplification using newly developed techniques applied to single cell RNA. Hybridization of single cell antisense RNA to cDNA or other oligonucleotide microarrays is used to determine expression profiles of known hydrodynamic shear stress responsive genes and a large number of other human and other mammalian genes, resulting in cell-specific mRNA expression profiles (e.g., transcriptional profiles) correlated with applied hydrodynamic forces in vitro or cells isolated from arteries. Genes associated with exposure to hydrodynamic forces, potentially including previously uncharacterized genes, are identified using the methods and compositions of the invention.

Manipulation of in vitro flow system parameters results in differential acute gene expression responses and chronic adaptive responses in cells exposed to disturbed or chaotic fluid flow, relative to cells exposed to undisturbed flow. These observations may be compared to identify the significance of spatial and temporal characteristics of the cell environment.

Association of atherosclerosis with flow characteristics (e.g., shear or shear gradients) may be used to predict association of atherosclerosis with characteristics of individual cells within a non-homogeneous monolayer.

Some cells removed from disturbed flow regions of anchored epithelia in vivo express an atheropermissive mRNA profile. Identification of this mRNA profile establishes an association between hydrodynamic stress exerted upon a vascular endothelial cell and the likelihood that the cell participates in regulatory events associated with the pathogenesis of an atherosclerotic lesion.

Endothelial cells lining the arterial circulation are exposed to fluid forces having greater magnitude than those experienced by cells in other mammalian tissues. Mechanisms responsible for transmission and transduction of hydrodynamic information from blood to a sub-epithelial layer of a blood vessel wall reside in the endothelium. A large body of evidence suggests that, during atherogenesis, normal physiological regulation of gene expression in cells of the vessel wall, including hemodynamic regulation, goes awry.

The present invention relates to assessment of endothelial gene expression as a function of the detailed (i.e., cellular or sub-cellular scale) local hydrodynamic environment in vivo and in vitro using micromanipulation techniques and high-throughput mRNA analysis at the single cell level. Heterogeneity of endothelial gene expression exists in different hemodynamically-defined regions of the arterial tree and between individual cells located within those regions. The methods of the invention include methods for assessing focal gene expression preceding lesion formation in order to identify genes associated with the onset of atherosclerosis.

According to one aspect of the present invention, in vitro differences in the surface geometry of endothelial cells within an apparently homogeneous monolayer and flow field are assessed in order to correlate cell-surface geometry and gene expression in the cells. The same individual cells and groups of cells can be removed by micromanipulation, and mRNA amplification and analysis, using, for example, array and microarray technology (cDNA and oligonucleotides) is performed. These procedures identify intercellular differences in gene expression and relate gene expression profiles to surface geometry and force distribution. These techniques can, for example, be used to investigate expression of athero-relevant genes that may also be hydrodynamically regulated. Such genes include PDGF, VCAM-1, ICAM-1, MCP-1, connexin43, tissue factor, and proteins of the thrombin receptor family. However, this approach is extended to the entire genome, particularly those genes/proteins involved in lipoprotein metabolism and cell-mediated redox mechanisms.

In another aspect of the present invention, in vitro gene expression in cells situated within a region of flow separation (i.e., precisely controlled disturbed flow) is investigated. The results of these investigations can be used to assess the effects of disturbed flow on surface geometry and to evaluate the consequence of such flow-affected geometry in terms of differential gene expression. This approach investigates flow-related effects in a two-dimensional flow field as a model for disturbed flow in vivo.

Figure 4A:
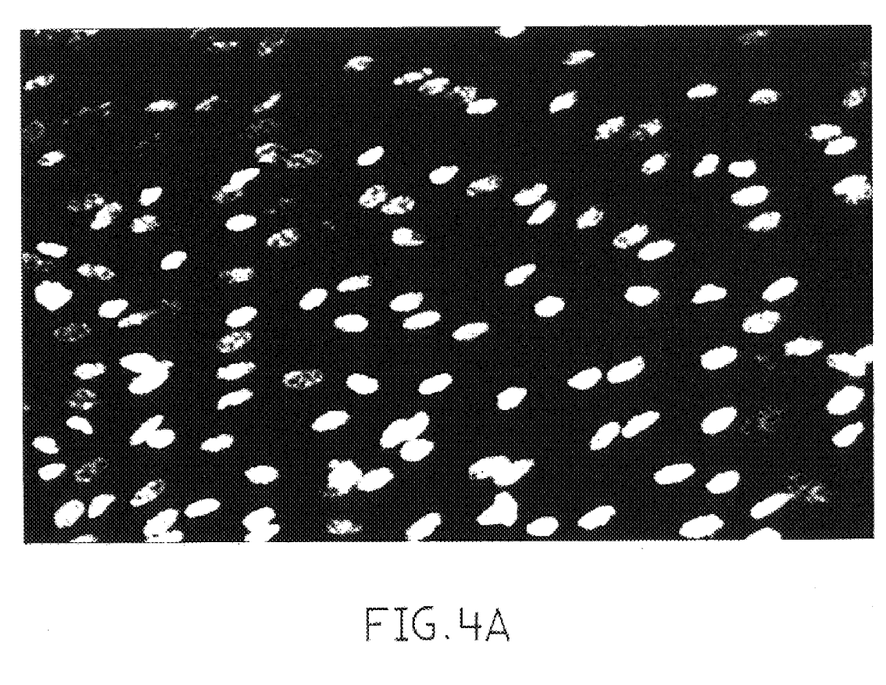
FIGS. 4A and 4B depict, respectively, a group of cells and a single cell (fluorescent nucleus) isolated from the artery wall by micropipette dissection.

In a third aspect of the present invention, focal endothelial gene expression is investigated in vivo in, for example, mammalian arteries. Single cells and groups of cells are removed from a vascular luminal endothelial tissue by micromanipulation. The tissue is preferably obtained from a region of flow disturbance and atherosclerosis-susceptibility throughout the arterial tree, as described in FIG. 4. These procedures assess the hemodynamic focal gene expression in vivo, and provide a gene expression profile data bank of selected atherosclerosis-prone regions of the arterial tree.

In a fourth aspect of the present invention, involvement of candidate genes which exhibit a differential pattern of expression in vivo in focal atherosclerotic lesion studies are evaluated in normal mammalian arteries and in murine models of atherosclerosis and hypertension. By way of example, mice which are nullizygous for genes encoding LDL receptor or apoE protein or mice used as known models of human atherosclerosis and hypertension are used. Furthermore, cells are removed for RNA amplification from fresh specimens of human arterial tissue obtained at surgery and candidate genes investigated by in situ hybridization and proteins by immunocytochemical analysis. Since mRNA amplification procedures have been demonstrated to work with single cells obtained from fixed tissue, arteries obtained at post-mortem locally and in the NIH Premature Development of Atherosclerosis in Youth study are assessed with regard to candidate gene expression.

Figure 1:
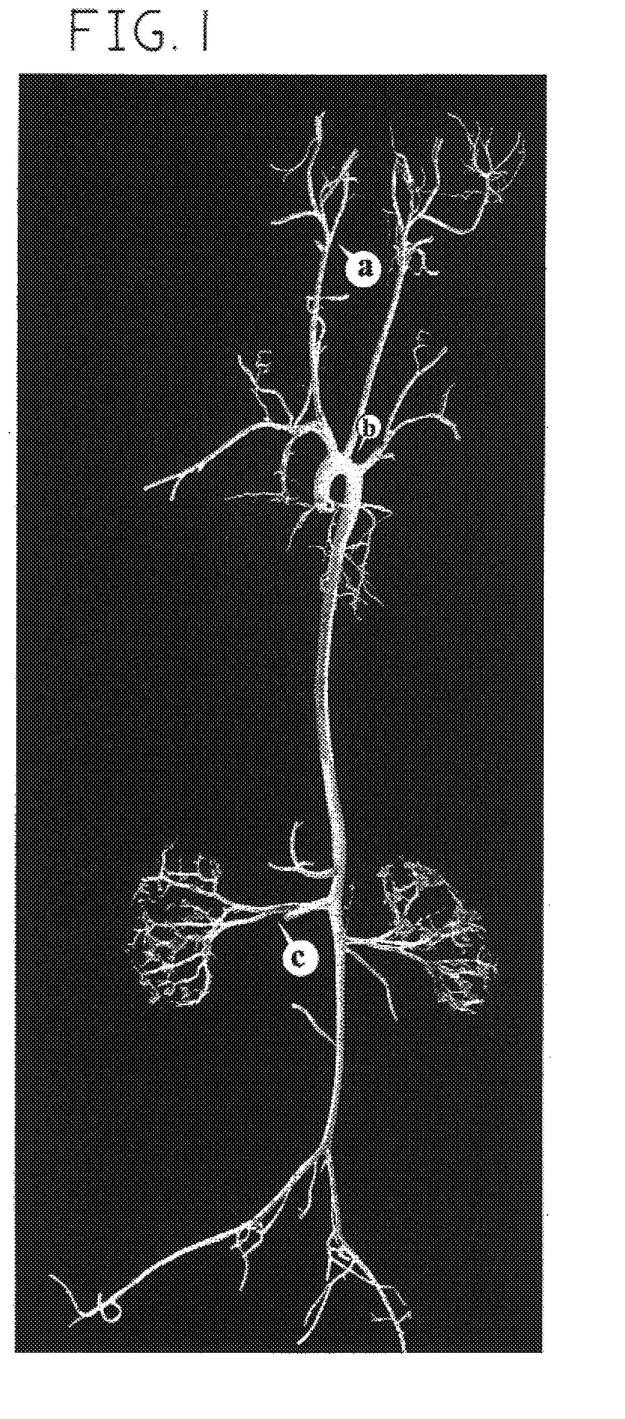
FIG. 1 is an image of a cast of a mouse arterial system typical of mammals (the heart was removed from the cast). Regions of flow separation are indicated by the arrow at position "a" indicating the carotid bifurcation, the arrow at position "b" indicating the aortic arch, and the arrow at position "c" indicating the renal branch artery. Curvatures, branches and bifurcations such as these positions are favored sites for the development of atherosclerotic lesions in humans and experimental animals.

In one embodiment, the invention includes a method of identifying a gene, wherein the level of expression of the gene is regulated by hydrodynamic stress. The method comprises obtaining a single endothelial cell or a group of cells from the vascular system of a mammal. In one embodiment, a single cell or a group of cells is isolated in vivo, as described herein, from a mammal at a vascular region which is prone to development of atherosclerotic focal lesions, as indicated in FIG. 1. In another embodiment, a single cell or a group of cells is obtained in vitro from a confluent monolayer of vascular endothelial cells, as described herein. In a preferred embodiment, a single arterial cell is isolated in vivo from a mammal at a vascular region which is prone to development of atherosclerotic focal lesions, as indicated in FIG. 1.

The method comprises subjecting the single cell or group of cells to hydrodynamic stress for a period of time and in an amount sufficient to regulate the level of expression of a gene. In one embodiment the single cell or group of cells is subjected to hydrodynamic stress using an in vitro flow chamber as described herein.

The in vitro flow chamber can, for example, be capable of generating a hydrodynamic stress flow field having spatially defined microheterogeneity determined by the geometry of the chamber, in a shear stress range from about −30 dyn/cm$^2$ (in flow reversal) to about +100 dyn/cm$^2$, corresponding to absolute values of from about 0 dyn/cm$^2$ to about 100 dyn/cm$^2$. Hydrodynamic stress field microheterogeneity results in different hydrodynamic stresses being exerted, in a predictable fashion, on various cells within the flow chamber. Use of such a chamber permits very fine spatial control of both hydrodynamic stress fields and the shear stress distribution gradient.

Hydrodynamic stress exerted upon cells in in vitro experiments can, for example, be in an amount from less than about 0.1 dyn/cm$^2$ to about 25 dyn/cm$^2$. In a preferred embodiment, the hydrodynamic stress exerted upon cells ranges from less than about 0.1 dyn/cm$^2$ to about 15 dyn/cm$^2$.

In the in vitro system, the hydrodynamic stress is exerted for a period of time of at least about several seconds. The period of time may range from about several seconds to about more than one week. In the in vivo system, the period of time may range from about several seconds to about one week, or up to the entire lifetime of the mammal. In a preferred embodiment, the hydrodynamic stress may be exerted for a period of time from about several seconds to about 3 days.

The method of the invention includes assessing the level of expression of a gene, after subjecting the cell or group of cells to hydrodynamic stress as described herein. A variety of techniques can be used to assess gene expression, including RT-PCR, and are known by the skilled artisan.

In a preferred embodiment, the level of expression of the gene is assessed using techniques such as northern blotting and microarray techniques after amplified antisense RNA as described herein.

In one embodiment, the level of expression of a gene is assessed using amplified antisense RNA in a group of endothelial cells isolated as described herein. In a preferred embodiment, the level of expression of the gene is assessed using amplified antisense RNA in a single endothelial cell, isolated as described herein.

The method of the invention also includes comparing the level of expression of the gene in a first vascular endothelial cell subjected to hydrodynamic stress with the level of expression of the same gene in a second endothelial cell from the vascular system of the mammal, which can be, for example, a similar or identical type of cell, which was subjected to different hydrodynamic stress (e.g., a second cell not subjected to hydrodynamic stress). Using this method, a gene is identified wherein the level of expression of the gene is regulated by hydrodynamic stress.

Also, the level of expression of a gene in a first group of cells which are subjected to hydrodynamic stress can be compared with the level of expression of the same gene in a second group of cells which are subjected to different hydrodynamic stress. The comparison can be made, for example, using a transcriptional profile which is, as described herein, generated using a radioactive probe or label or a fluorescent probe or label. Other techniques for comparing levels of expression of a gene are known to the skilled artisan, and such techniques are included in the methods of the invention. The comparison of expression levels of the gene can be made using any of the methods described herein or known to the skilled artisan.

In another embodiment, the level of expression of many genes is compared using a transcriptional profile obtained from a single cell or from a group of cells after northern blotting or microarray analysis using a radiolabeled or fluorescent probe as described herein.

The invention also includes a method of identifying a nucleic acid comprising a hydrodynamic stress regulation (HSR) region. The method includes subjecting a first vascular endothelial cell of a mammal to hydrodynamic stress, as described herein. The method includes thereafter assessing the level of expression of the nucleic acid in the cell using any of the methods described herein for assessing the level of expression of a gene. The method further includes comparing the level of expression of the nucleic acid in the first cell with the level of expression of the same nucleic acid in a second vascular endothelial cell of the mammal, the second cell being subjected to different hydrodynamic stress. Such comparisons are made as described herein for comparing levels of expression of a gene. Using this method, a difference between the level of expression of the nucleic acid in the first cell and the level of expression of the nucleic acid in the second cell is an indication that the nucleic acid comprises a HSR region.

In another aspect, the invention includes a method of identifying a nucleic acid comprising a hydrodynamic stress regulation (HSR) region by comparing the sequence of a first nucleic acid with the sequence of a second nucleic acid comprising a hydrodynamic stress regulation (HSR) region. In this method, the second nucleic acid comprises a hydrodynamic stress regulation (HSR) region of known sequence. The method includes identifying a region of the first nucleic acid which is homologous to the HSR region of the second nucleic acid using a technique for comparing nucleic acid sequences and identifying homologous regions. Such techniques are known to the skilled artisan. Using this method, a nucleic acid comprising a HSR region is identified.

Also included in the invention is a method of identifying a hydrodynamic stress responsive protein encoded by a nucleic acid. The method comprises subjecting a first vascular endothelial cell of a mammal to hydrodynamic stress as described herein. Thereafter, the level of expression of the nucleic acid in the cell is assessed as described herein. A comparison is then made between the level of expression of the nucleic acid in the first cell with the level of expression of the same nucleic acid in a second vascular endothelial cell of the mammal, the second cell being subjected to different hydrodynamic stress. Such a comparison between levels of nucleic acid expression is also made as described herein. A difference discerned between the level of expression of the nucleic acid in the first cell and the level of expression of the nucleic acid in the second cell is an indication that the nucleic acid encodes a hydrodynamic stress responsive protein.

The method further includes identifying a protein encoded by the nucleic acid, thus identifying a hydrodynamic stress responsive protein. Techniques for identifying a protein encoded by a nucleic acid are known to the skilled artisan. Such techniques include, for example, deriving the amino acid sequence of a protein encoded by a nucleic acid from the nucleotide sequence of the nucleic acid, and identifying a protein having the derived amino acid sequence using a protein sequence databank.

Another aspect of the invention is an array of nucleic acids comprising a HSR region, wherein at least one of the nucleic acids is selected by the method described above for identifying a nucleic acid comprising a HSR region.

The invention also includes a kit for identifying a gene, the expression of which is regulated by hydrodynamic stress. Such a kit may include, for example, a reagent for use in amplified antisense RNA, a reagent for use in northern blotting or microarray analysis, and a radiolabeled or fluorescent probe.

The invention is further described in detail by reference to the following examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

EXAMPLE 1

Atomic force imaging of single cells and groups of cells in vitro, and recently in arterio, and associated computational fluid dynamics have previously been described (Barbee et al., 1995, Am. J. Physiol. 268:H1765–H1772).

Various in vitro disturbed flow chambers, such as those described herein, are known and may be used in the methods of the invention.

Micromanipulation techniques to remove single cells from in vitro flow fields and from arterial walls, are described herein. Microdissection of cooled, unfixed mammalian arterial tissues to obtain single cells (see FIG. 4B) is routine. Silver staining of the mammalian endothelium in hemodynamically relevant regions can be performed as described herein. Furthermore, in situ hybridization and immunocytochemical procedures using a variety of cells and tissues are known in the art.

The single cell mRNA amplification techniques for neuronal cells used herein has previously been described (Eberwine et al, 1992, Methods in Enzymology 216:80–100). This technique was adapted, as described herein, for use with vascular endothelial cells. High throughput mRNA screening of human endothelial RNA is performed using microarrays.

Living Cell Surface Geometry

The experiments described herein expand upon previous cell imaging studies (Barbee et al., 1995, Am. J. Physiol. 268:H1765–H1772; Davies et al., 1995 Physiol. Rev. 75:519–560; Davies et al., 1997, Ann. Rev. Physiol. 59:527–549) which demonstrated that the presence of endothelial cells in a flow field results in microscopic differences in shear stress magnitude and distribution from those calculated for a flat boundary. These differences, in turn, caused a localized perturbation of the macroscopic flow field. From the point of view of the endothelial cell, the shear stress at the lumenal surface varied microscopically within the macroscopic flow field as a function of the surface geometry. The topographic variations from cell to cell and the consequent effects upon shear stress distribution for cells in culture were described in Barbee et al. (1995, Am. J. Physiol. 268:H1765–H1722). The surface topography of living endothelium in the artery wall was described in Davies et al. (1995, J. Biomech. 28:1459–1469).

A comparison of endothelial geometry in vitro versus in situ demonstrated close similarities, supporting extension of the hypothesis of endothelial heterogeneity to in vivo flow fields. Thus, cells in certain morphological configurations are likely to be exposed to much lower or higher shear stress gradients than neighboring cells. Highly variable individual cell responses to uniform flow result from cells being above or below threshold levels necessary to elicit a bioresponse to the flow field. For example, in aligned cells there was an approximately 40% decrease in the average shear stress gradients compared with no-flow control cells.

Creation of Disturbed Flow in vitro

Figure 3A:
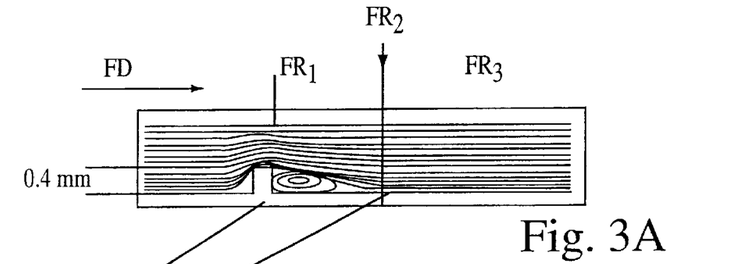
FIG. 3A is a schematic depiction of a flow chamber. The direction of flow is indicated by the horizontal arrow. Streamlines indicate regions of flow separation, recirculation, reattachment and recovery. Endothelial cells were grown to confluence in various regions (identified above the chamber) of the chamber from the flow barrier (indicated at the bottom of the chamber by the rectangle having an 0.4 mm long-axis perpendicular to the direction of flow) to the flow recovery region.
Figure 3B:
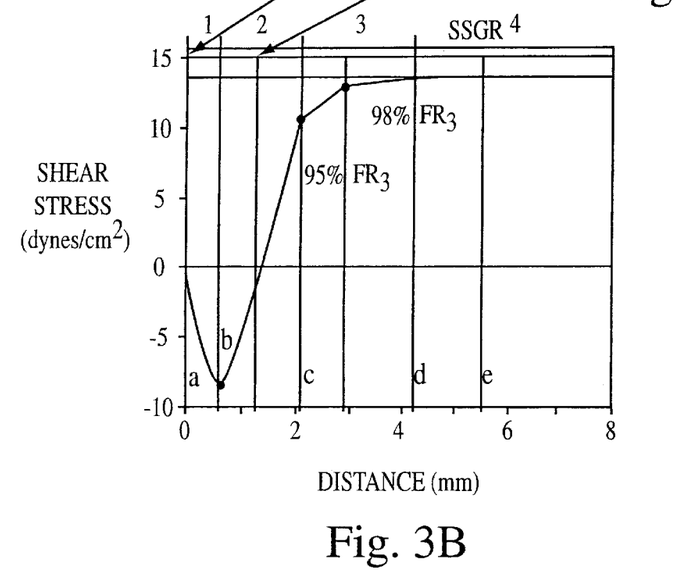
FIG. 3B is a graph depicting the shear stress distributions at the coverslip surface upon which cells were cultured in the flow chamber.
Figure 3C:
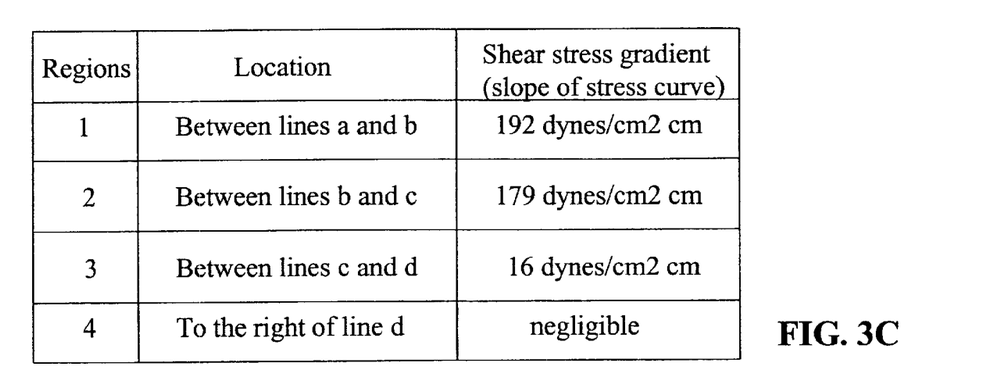
FIG. 3C is a table depicting Shear Stress Gradient Regions (SSGR), indicating the locations and slope of the stress curve in regions 1–4 depicted in FIGS. 3A and 3B.

Systems that realistically simulate the flow separation, recirculation zones, and reattachment that occur in vivo were developed. The latest version of the system is a disturbed flow chamber apparatus illustrated in FIG. 3A (DePaola et al., 1999, Proc. Natl Acad. Sci. USA 96:3154–3160). This apparatus provided precise control of the spatial distribution of macroscopic shear stresses throughout the flow field. It consisted of a flow loop connected to a parallel plate chamber in which a 22 millimeter square glass coverslip with a surface step is placed and upon which a confluent monolayer of endothelial cells was grown. The rectangular step on the coverslip surface (located upstream from cells with its largest dimension perpendicular to the flow) created a localized region of flow separation and recirculation (flow disturbance) within the chamber. The channel height in the flow chamber was much less than its width. Therefore, the flow was considered two-dimensional. Further downstream of the step, the full-developed laminar flow had a parabolic velocity profile and uniform wall shear stress. The distribution of shear stress in this system is indicated in FIG. 3B.

In one set of experiments, pulsatile flow was introduced into the system, as a model of the complexity of the disturbed flow field in vivo. Computational fluid dynamic calculations of such complex fields can be made, and topographic and gene regulatory changes in endothelial cells can be documented.

In vivo Imaging

As documented elsewhere herein, determination of ultrasound and magnetic resonance angiography may be used to verify regions of disturbed flow in mammalian arteries. Primate/human sized imaging is relatively routine.

Micromanipulation in vitro and in situ

Using micropipets (1–10 micrometer diameter) and micromanipulators single endothelial cells were removed from confluent cells in culture. Single cells were transferred directly to eppendorf tubes containing an amplification cocktail. Direct visual observation of the procedure to obtain spatially-defined individual cells from the flow chambers provided assurance that the gene expression profile (i.e., transcriptional profile) represented the particular cell in subsequent analysis.

Figure 2:
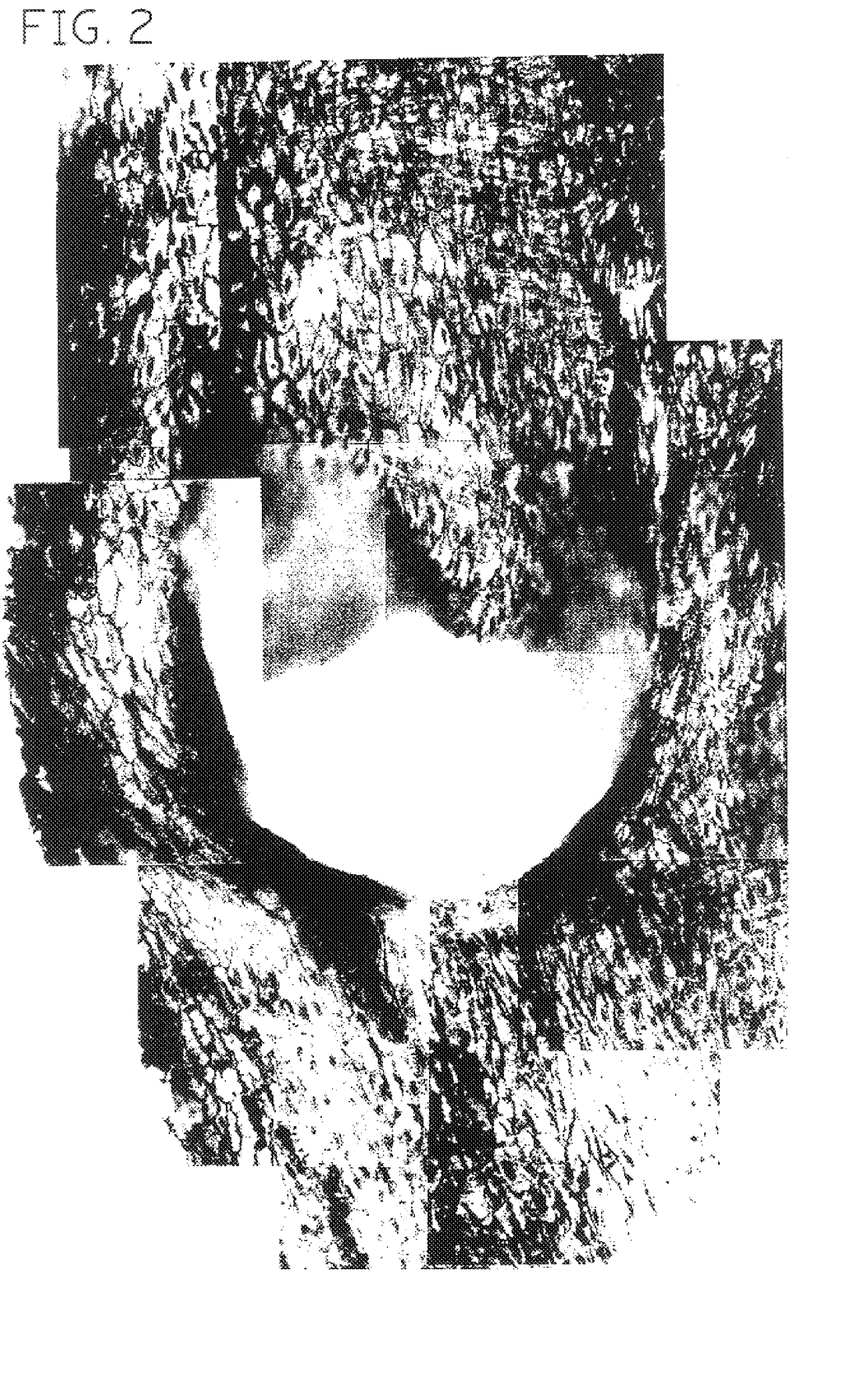
FIG. 2 is an image of a silver-stained mouse arterial endothelium showing a variety of endothelial cell shapes indicative of the variable hemodynamic environment adjacent to a branch artery (center white region).

The isolation of single endothelial cells and groups of endothelial cells from intact arteries was performed in a similar manner. Several approaches may be used to identify, on morphological grounds, cells located in different flow regions. One useful approach is to gently infuse a fluorescent nuclear stain (e.g., Hoechst stain #33258, Sigma Chemical Co., St. Louis, Mo.) into the arterial lumen for thirty seconds followed by a wash perfusion. Individual fluorescent endothelial cell nuclei were observed by epi-illumination using a DAPI filter (365 nanometer excitation wavelength, lp 420 nanometer emission wavelength) without the need for transillumination. In thinner-walled arteries (e.g., mouse) silver staining of the endothelium reveals cell morphology (e.g., FIG. 2) indicative of local flow conditions. Alternatively, cells may be obtained from regions that are clearly representative of disturbed or developed flow regions (i.e., athero-susceptible or athero-resistant regions).

Amplified Antisense mRNA in Single Endothelial Cells

In order to test the feasibility of amplification of mRNA obtained from single endothelial cells, the following procedure was performed. Single endothelial cells were obtained from a cultured monolayer and frozen/thawed to lyse the cells. An oligo(dT) primer extended at the 5' end with a T7 RNA polymerase promoter was synthesized. This oligonucleotide was used to prime the poly $(A)^+$ mRNA population for cDNA synthesis. The oligonucleotide primer, RNase inhibitor (Rnsin), dNTP's, reverse transcriptase (RT), and RT buffer were added to the cell lysis solution, and then incubated for 1 hour at 37° C. to synthesize first strand cDNA.

The resulting first strand cDNA-mRNA hybrid was ethanol precipitated, mRNA digested away with RNase H, and second strand DNA synthesis accomplished by the addition of RNase H buffer, RNase H, DNA polymerase I, and Klenow. Following one hour of incubation at room temperature, the solution was heated to 65° C. in order to inactivate the enzymes. Double stranded DNA (containing a T7 RNA polymerase promoter site) was ethanol precipitated.

The double stranded DNA was re-suspended in TE buffer, heat denatured, and combined with a mixture or rNTP's, DTT, transcription buffer, DEPC water, and T7 RNA polymerase. The reaction mixture was incubated for one hour at 37° C., and then RNA was purified using phenol-chloroform and ethanol precipitated. RNA concentration was spectrophotometrically determined ($OD_{260}$).

This RNA was then subject to a second reverse transcriptase reaction, as described above, followed by the purification steps and a second transcription reaction to further amplify the mRNA population. The resulting mRNA was amplified to achieve an approximately million-fold increase over the initial RNA content. The distribution of mRNA sizes as assessed by agarose gel electrophoresis (range of approx. 600 to >5,000 nucleotide residues), suggested that large mRNA amplification was representative of the starting material. This approach therefore provided a valid representation of mRNA expression in small groups of endothelial cells.

Disturbed Flow Experiments

The parallel plate flow chamber consisted of a Teflon upper plate and a stainless steel bottom plate held together by 8 screws. A medical-grade silicon gasket sealed the chamber and prevented fluid leakage. A precisely machined recess (1×30×120 millimeters) in the top plate defined the flow path in the chamber. The top plate also housed the inlet and outlet ports and a quartz window for light transmission.

The bottom plate was machined flat and polished to a mirror finish with an opening 62 millimeters from the flow entrance for sample placement. Endothelial cells were grown on 22 millimeter square glass coverslips onto which a steel frame with a rectangular step 30 millimeters long, 1 millimeter wide and 0.2 or 0.4 millimeters high (flow disturbance) was bonded. The step overlaps the glass coverslip by 4 millimeters on each side to minimize flow edge effects. The steel frame was positioned on the flow chamber so that the glass surface was continuous with the bottom surface of the flow channel. The design avoided any mechanical injury to the endothelial monolayer during loading into the apparatus.

The glass coverslips (Bellco Glass, Inc., Vineland, N.J.) contained a fine photoetched grid (600 microns square) that facilitated correlation of monolayer morphological alteration and mRNA expression with spatial distribution of calculated wall shear stress forces. Flow was imposed on the endothelial surface by connecting the parallel plate chamber to a flow circuit which consisted of a variable speed peristaltic pump, a fluid capacitor that dampened any pulsation of the flow caused by the pump, and a fluid reservoir for recirculation. The reservoir and the fluid capacitor were kept in water baths to maintain culture medium at 37° C. The pH and oxygen tension in the medium were maintained by a 95% air 5% (v/v) $CO_2$ humidified gas mixture blown over the fluid surface in the reservoir. The flow chamber was positioned on the mechanical stage of an inverted phase microscope allowing continuous visualization of cell monolayers. All surfaces of the device in contact with the fluid were pre-sterilized.

Determination of Flow Characteristics

In the parallel plate apparatus modified for disturbed flow, the shear stress in regions of fully developed laminar flow downstream from the disturbed region is given by $$\tau = 6\,\mu U/H$$

where U is the mean velocity of the flow through the channel, H is the channel height, and $\mu$ is the dynamic viscosity of the fluid. The Reynolds number characterizing the flow in the parallel-plate chamber is given by $$Re = UH/v$$

where v is the kinematic viscosity of the fluid. In the disturbed flow region, the wall shear stress is non-uniform. The spatial variation in shear stress in regions of flow separation and recirculation (flow disturbance) was obtained from the numerical solution of the flow equations as described below.

Finite element models were used to calculate the local flow characteristics and the spatial distribution of the fluid forces on the cell layers. The computational domain was a two dimensional straight channel with a rectangular step on one of the walls. The aspect ratio of the step (h/L) was 0.4 and the ratio of the channel gap to the step height (H/h) was 2.5. Two-dimensional steady state Navier-Stokes equations were solved using the computational program NEKTON (Maday et al., 1989, In "State of the Art Surveys on Computational Mechanics," Eds. Noor et al., Publ. Am. Soc. Microbiol., Wash. D.C., 71–143). NEKTON employs spectral element partial discretization in which the spatial resolution is characterized by the number and placement of the spectral elements (computational sub-domains) and the choice of order (N) of the polynomial expansions used to generated the global discrete equations within each sub-domain. In order to resolve the details of flow separation and reattachment, the smallest domain (grid) spacing was used behind the step, the region of highest gradients. The boundary conditions used to solve the equations were: a) non-slip condition at the channel surfaces, b) a fully developed Poiseuille velocity profile at the inflow, and c) at the outflow, the requirement that the same mass flow rate exits the computational domain as enters it.

On the basis of these calculations, fluid flow through the chamber (Q) and the medium viscosity ($\mu$) were adjusted to produce regions of flow separation, reattachment and flow recovery over the same endothelial monolayer at physiological levels of shear stress.

EXAMPLE 2

The experiments of this Example address the hypothesis that the effect of hydrodynamic stress upon the level of expression of a limited number of genes in even only a few endothelial cells can dominate vascular physiology and vascular pathogenesis. This was accomplished using the amplified antisense mRNA technique to characterize gene expression in cardiovascular endothelium. Quantitative profiles of gene expression (i.e., transcriptional profiles), were used to assess endothelial heterogeneity in a detailed (single cell) yet comprehensive (multiple genes, high-throughput) approach which should increase the probability of finding new therapeutic targets for the treatment and prevention of cardiovascular diseases such as atherosclerosis. The use of high-throughput hybridization methods in this approach allowed simultaneous screening of many genes.

Amplified Antisense mRNA in Single Cells or Small Groups of Cells

An adaptation of a known amplified antisense RNA technique (Eberwine et al., 1992, Proc. Nat. Acad. Sci. USA, 89:3010–3014) was used to obtain mRNA from cardiovascular endothelial cells in order to amplify and characterize transcripts from single cells and small groups of endothelial cells in spatially-relevant cardiovascular locations. This technique provided near-linear amplification of the original mRNA population of the cell, in contrast to RT-PCR, which is unable to amplify all messages accurately due to nucleotide misincorporations which occur during the exponential amplification process and also due to a bias towards smaller cDNA sizes.

Figure 5:
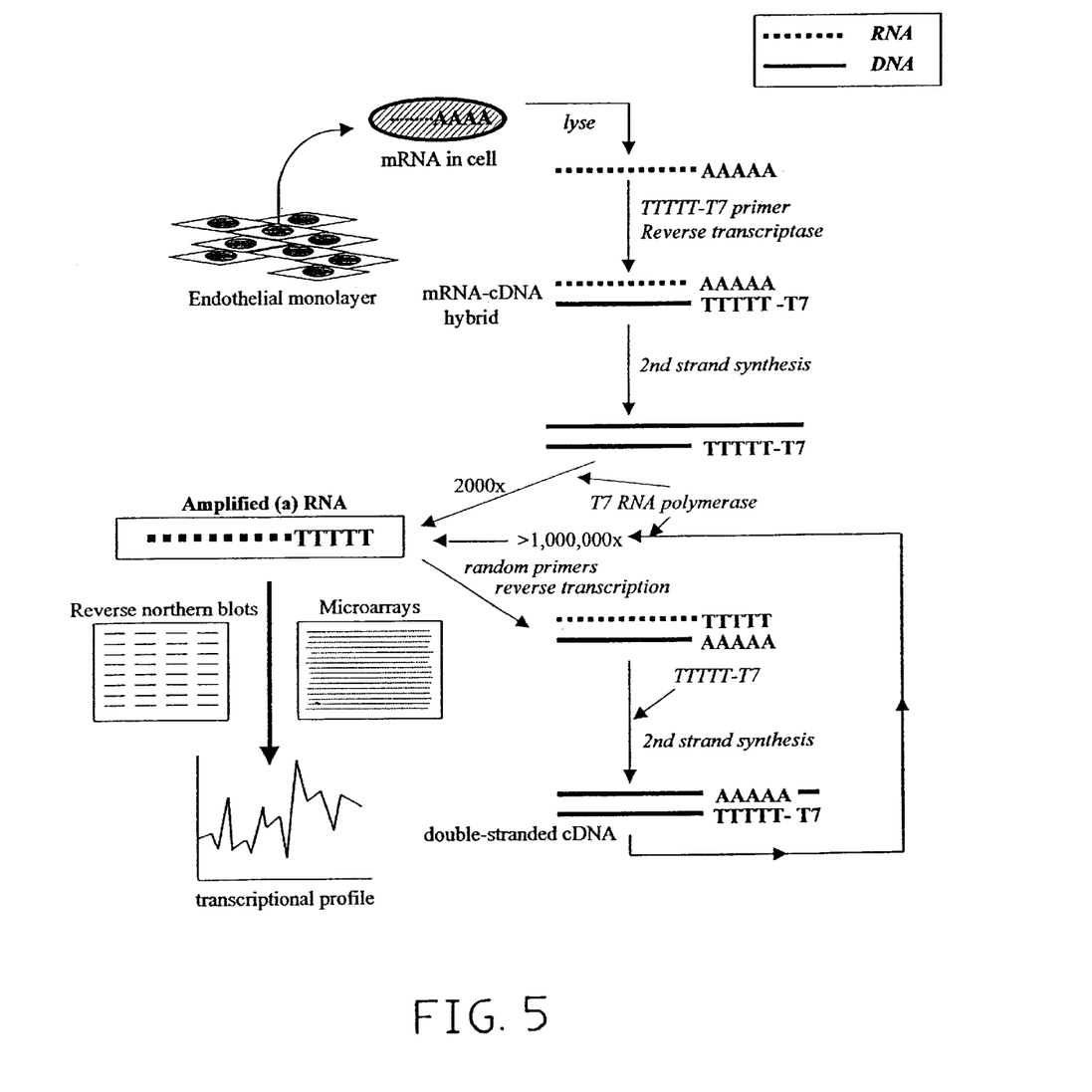
FIG. 5 is an illustration of a method for amplification of single cell RNA (from Eberwine et al., 1992, Proc. Nat. Acad. Sci. USA 89:3010–3014) adapted as described herein for cardiovascular cells.

The initial mRNA population was amplified as depicted in FIG. 5. Briefly, a reverse-transcriptase reaction was used to generate cDNA from the initial mRNA population. A T7 RNA polymerase promoter site was incorporated into each cDNA copy generated from the original mRNA using an oligo-dT-T7 primer. The single stranded cDNA was made double stranded using standard techniques as described herein to provide a functional T7 RNA polymerase promoter site from which antisense RNA was transcribed. This permitted individual mRNAs to be linearly amplified (approximately 2000-fold) in proportion to their abundance. The antisense RNA was then subjected to a second round of reverse transcription followed by double-stranded cDNA synthesis. Transcription in the presence of either radiolabeled (for reverse northern blots) or fluorescent-tagged (for DNA chip array screening; see, e.g., Schena et al., 1995, Science, 270:467–470; DeRisi et al., 1996, Nat. Genet., 14:457–460). rNTPs resulted in generation of an mRNA population wherein each mRNA molecule comprised a detectable label. Typically, a one-million-fold amplification of antisense RNA (relative to the starting material) was achieved following two rounds of amplification from a single cell.

The mixture of antisense RNAs was hybridized with cDNA species immobilized on reverse northern blots. Alternatively, microarrays are used. The autoradiographic or fluorescence signal corresponding to each cDNA spot (normalized to a control gene or a "spiked" internal RNA control, e.g., bacterial RNA) represented the abundance of the corresponding mRNA in the antisense RNA population. A difference in signal intensity of a factor of two or greater for large RNAs was considered significant.

Single Endothelial Cell Transcriptional Profiling

Figure 6:
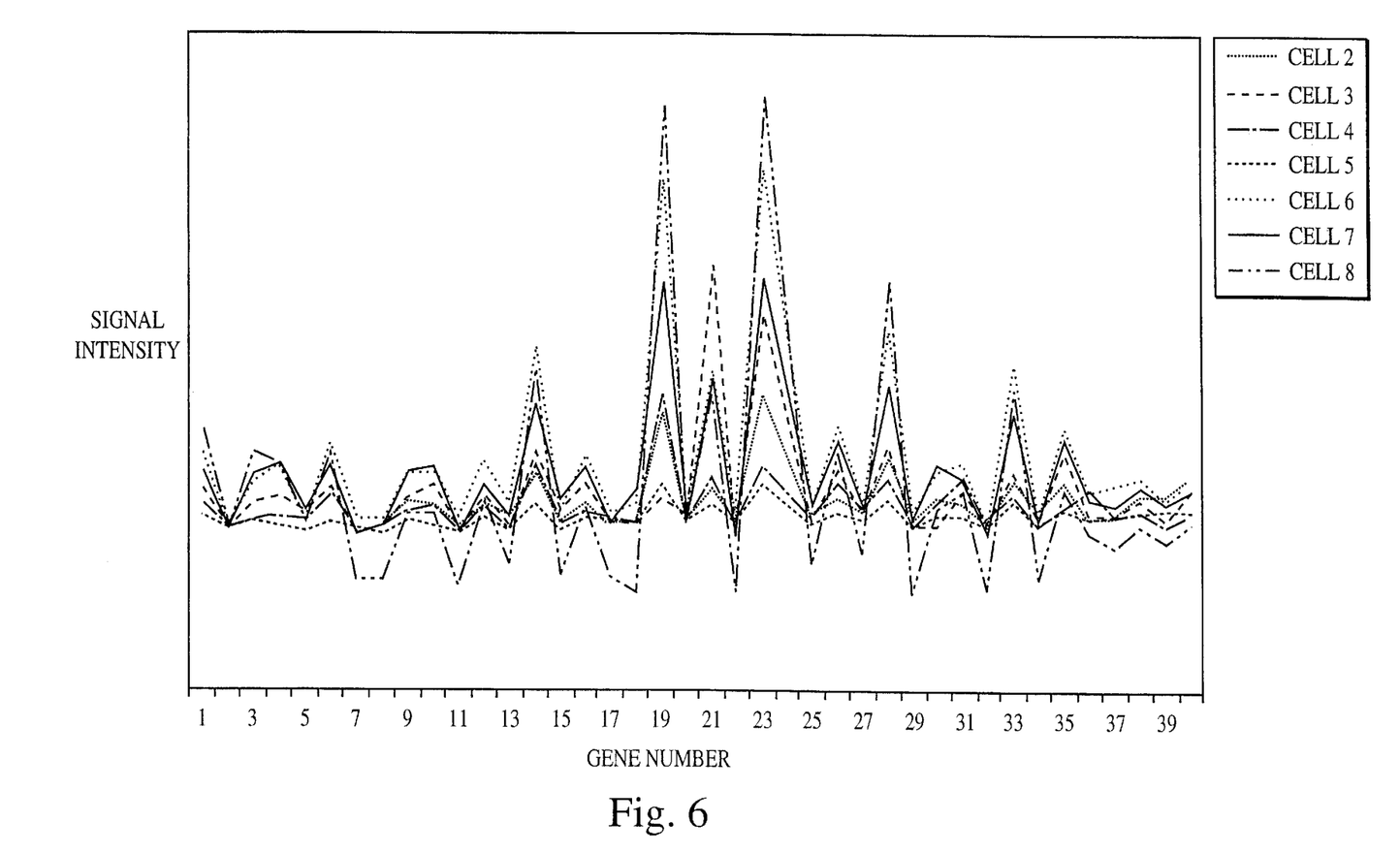
FIG. 6 is a graph depicting transcriptional profiles for 40 different genes of seven individual endothelial cells (designated cells 2–8) removed from monolayers after 16 hours of exposure to steady flow in vitro at 13 dyn/cm$^2$ shear-stress. The names and GenBank Accession number of each of genes 1–40 are indicated in Table 1 herein.

The same amplified antisense RNA technique was used to generate transcriptional profiles for each of 40 genes in seven morphologically-identical endothelial cells individually dissected from a confluent monolayer following 16 hours of exposure to 13 dynes per square centimeter unidirectional shear stress. FIG. 6 depicts the results of these experiments.

Although the overall transcriptional profiles were similar for each of the seven cells, variations in expression levels of individual genes varied by as much as five-fold. The identity of each of genes 1–40 is listed in Table 1. Expression levels were normalized by reference to a control plasmid signal at position 2 depicted in FIG. 3B. Triplicate amplifications from single cells yielded expression levels that varied by no more than 30%.

Figure 4B:
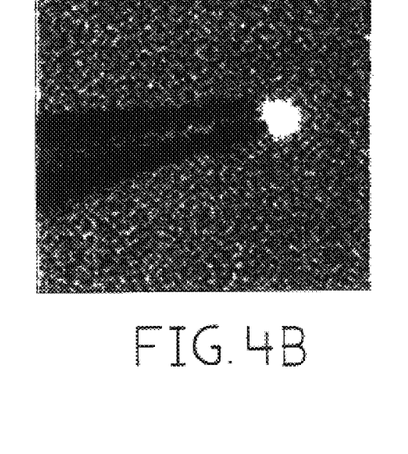
Figure 4C:
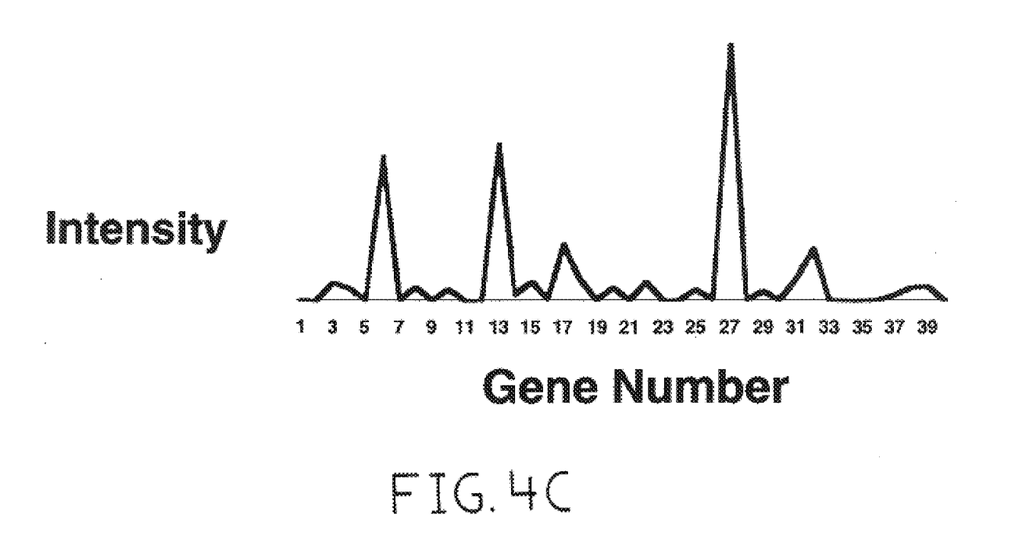
FIG. 4C depicts a transcriptional profile obtained as described herein from the single cell depicted in FIG. 4B.
Figure 7:
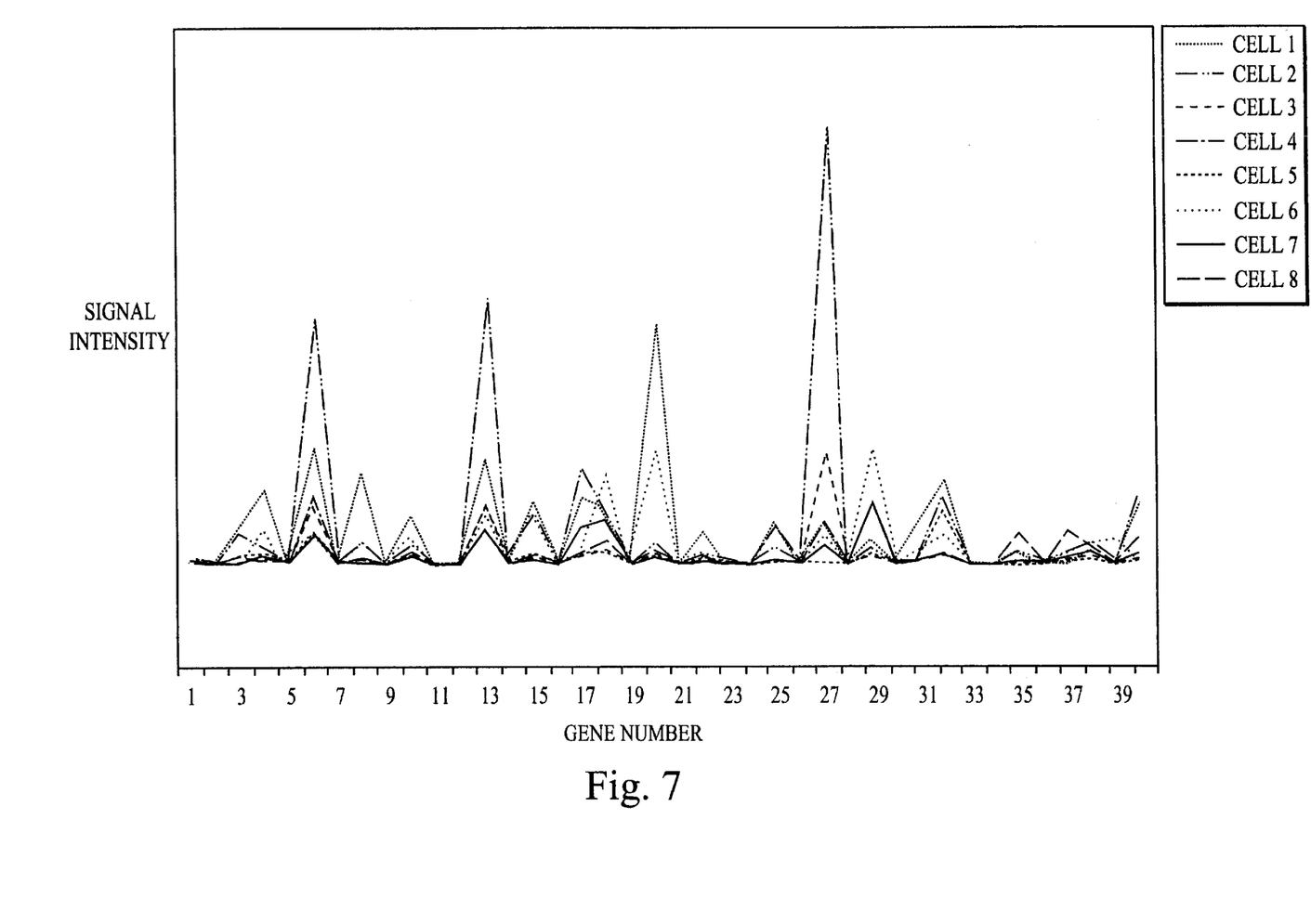
FIG. 7 is a graph depicting transcriptional profiles of eight individual endothelial cells isolated from a swine artery using the approach described in FIG. 4.

In another set of experiments, single endothelial cells were isolated from swine artery as described in FIG. 4B using the methods described herein and subjected to the amplified antisense RNA procedures described herein. Levels of gene expression were compared as described herein using transcriptional profiles. Data from these experiments are shown in FIG. 7.

The results of all of the experiments presented in this Example indicate that gene expression can be quantified at the single cell level and that a cell-by-cell analysis can be conducted as a function of cell location in a defined flow field. Using this method, expression levels of genes in individual cells can be compared. Also, the transcriptional profile of many genes can be compared on a cell-by-cell basis or a region-by-region basis as an average profile in order to detect multi-gene changes and potential interactive relationships. Thus, this method allows precise spatial determination of gene expression in tissue(s). As demonstrated in this Example in the context of hemodynamics, gene expression can be assessed in distinguishable portions of a single tissue using multiple gene detection assays, such as a few, dozens, or even thousands of cDNAs and ESTs using the methods described herein.

TABLE 1

Identification of Genes 1–40 in FIG. 6.

| Gene | GenBank Accession # |
| --- | --- |
| 1. Beta-Actin | M10277 |
| 2. Bluescript | |
| 3. Bax | NM-004324 |
| 4. ApoE | M73490 |
| 5. IL-12P35 | M86672 |
| 6. Vcam | X53051 |
| 7. Endothelin | Y00749 |
| 8. IL-6 | M26744 |
| 9. CD44 | U40373 |
| 10. MIG | M34815 |
| 11. CXcr4 | AF025375 |
| 12. c-jun | X17163 |
| 13. PKC-1b | X07286 |
| 14. MCP-1 | X14768 |
| 15. Rantes | M21121 |
| 16. Cx43 | J05535 |
| 17. Creb | X14788 |
| 18. Ubiquitin | M26880 |
| 19. PDGF-b | X02744 |
| 20. KC | M86536 |
| 21. Vimentin | NM-003380 |
| 22. Trkb | X76473 |
| 23. PARI | AF084645 |
| 24. TNF-alpha | X66539 |
| 25. MIP-1beta | U06434 |
| 26. eNOS | M89952 |
| 27. IL-1b | X65019 |
| 28. PAR2 | AF084644 |
| 29. iNOS | L09126 |
| 30. GAPDH | AF106860 |
| 31. CNP | NM-000753 |
| 32. BDNF | NM-001709 |
| 33. PAR3 | U92971 |
| 34. Stromelysin | X64020 |
| 35. MIP-1alpha | U22414 |
| 36. Fos | K00650 |
| 37. BCL-2 | L14680 |
| 38. Aldolase | M11560 |

TABLE 1-continued

Identification of Genes 1–40 in FIG. 6.

| Gene | GenBank Accession # |
|---|---|
| 39. TIMP | NM-003254 |
| 40. IP-10 | U22520 |

The disclosures of each and every patent, patent application and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

We claim:

1. A method of identifying a gene, expression of which is regulated by hydrodynamic stress, the method comprising
    a) subjecting a first vascular endothelial cell of a mammal to hydrodynamic stress using an in vitro flow chamber;
    b) thereafter assessing the level of expression of the gene in the cell; and
    c) comparing the level of expression of the gene in the first cell with the level of expression of the same gene in a second vascular endothelial cell of the mammal, the second cell being subjected to different hydrodynamic stress;
whereby a difference between the level of expression of the gene in the first cell and the level of expression of the gene in the second cell is an indication that the gene is regulated by hydrodynamic stress.

2. The method of claim 1, wherein the flow chamber is capable of generating a hydrodynamic stress flow field having spatially defined microheterogeneity.

3. The method of claim 2, wherein the microheterogeneity results in different hydrodynamic stresses exerted from one cell to another or from one part of a cell to another part of a cell in the flow chamber.

4. The method of claim 1, wherein the mammal is a human.

5. The method of claim 1, wherein the hydrodynamic stress is exerted in an amount from about 0 dyn/cm$^2$ to about 100 dyn/cm$^2$.

6. The method of claim 1, wherein the hydrodynamic stress is exerted for at least about several seconds.

7. The method of claim 1, wherein the cell is a single cell isolated in vivo.

8. The method of claim 7, wherein the cell is an arterial endothelial cell.

9. The method of claim 1, wherein a group of cells is isolated in vivo.

10. The method of claim 1, wherein the cell is a single cell isolated in vitro from a confluent monolayer.

11. The method of claim 1, wherein the cell is one of a group of cells isolated in vitro from a confluent monolayer.

12. The method of claim 1, wherein the level of expression of the gene is assessed using amplified antisense RNA in combination with northern blotting or a microarray technique.

13. The method of claim 12, wherein the level of expression of the gene is assessed in a single endothelial cell.

14. The method of claim 12, wherein the level of expression of the gene is assessed in one of a group of endothelial cells.

15. The method of claim 12, wherein the level of expression of the gene is compared by transcriptional profiling following one of northern blotting and microarray analysis using one of a radiolabeled probe, a fluorescent probe, and a label.

16. The method of claim 12, wherein the levels of expression of a plurality of genes are compared.

17. A method of identifying a nucleic acid comprising a hydrodynamic stress regulation (HSR) region, the method comprising
    a) subjecting a first vascular endothelial cell of a mammal to hydrodynamic stress using an in vitro flow chamber capable of generating a hydrodynamic stress flow field having spatially defined microheterogeneity;
    b) thereafter assessing the level of expression of the nucleic acid in the cell; and
    c) comparing the level of expression of the nucleic acid in the first cell with the level of expression of the same nucleic acid in a second vascular endothelial cell of the mammal, the second cell being subjected to different hydrodynamic stress;
whereby a difference between the level of expression of the nucleic acid in the first cell and the level of expression of the nucleic acid in the second cell is an indication that the nucleic acid comprises a HSR region.

18. The method of claim 17, wherein the level of expression of the nucleic acid is assessed using amplified antisense RNA from a single endothelial cell.

19. A method of identifying a nucleic acid comprising an HSR region, the method comprising
    a) comparing the sequence of a first nucleic acid with the sequence of a second nucleic acid comprising an HSR region, the second nucleic acid being identified by method of claim 17; and
    b) identifying a region of the first nucleic acid which is homologous to the HSR region of the second nucleic acid, whereby a nucleic acid comprising a HSR region is identified.

20. A method of identifying a hydrodynamic stress responsive protein, the method comprising
    a) subjecting a first vascular endothelial cell of a mammal to hydrodynamic stress using an in vitro flow chamber capable of generating a hydrodynamic stress flow field having spatially defined microheterogeneity;
    b) thereafter assessing the level of expression of a nucleic acid in the first cell;
    c) comparing the level of expression of the nucleic acid in the first cell with the level of expression of the same nucleic acid in a second vascular endothelial cell of the mammal, the second cell being subjected to different hydrodynamic stress, whereby a difference between the level of expression of the nucleic acid in the first cell and the level of expression of the nucleic acid in the second cell is an indication that the nucleic acid encodes a hydrodynamic stress responsive protein; and
    d) identifying a protein encoded by the nucleic acid, whereby a hydrodynamic stress responsive protein is identified.

21. The method of claim 20, wherein the level of expression of the nucleic acid is assessed in a single endothelial cell.

22. A method of making an array of nucleic acids comprising an HSR region, the method comprising
  a) selecting a plurality of nucleic acids comprising an HSR region by method of claim 19; and
  b) incorporating the selected nucleic acids into an array.

23. A kit for carrying out the method of claim 2, the kit comprising
  a) an instructional material describing use of the kit for the method of claim 2;
  b) a reagent for use in amplified antisense RNA;
  c) a reagent for use in northern blotting or microarray analysis; and
  d) a radiolabeled or fluorescent probe.

24. The method of claim 17, wherein the mammal is a human.

25. The method of claim 19, wherein the mammal is a human.

26. The method of claim 20, wherein the mammal is a human.

* * * * *